US009984278B2

United States Patent
Needleman et al.

(10) Patent No.: US 9,984,278 B2
(45) Date of Patent: May 29, 2018

(54) NON-LINEAR IMAGING SYSTEMS AND METHODS FOR ASSISTED REPRODUCTIVE TECHNOLOGIES

(71) Applicant: PRESIDENT AND FELLOWS OF HARVARD COLLEGE, Cambridge, MA (US)

(72) Inventors: Daniel Needleman, Somerville, MA (US); Manqi Deng, Natick, MA (US); Timothy H. Sanchez, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 83 days.

(21) Appl. No.: 15/304,173

(22) PCT Filed: Apr. 16, 2015

(86) PCT No.: PCT/US2015/026123
§ 371 (c)(1),
(2) Date: Oct. 14, 2016

(87) PCT Pub. No.: WO2015/161045
PCT Pub. Date: Oct. 22, 2015

(65) Prior Publication Data
US 2017/0039415 A1     Feb. 9, 2017

Related U.S. Application Data

(60) Provisional application No. 61/980,508, filed on Apr. 16, 2014.

(51) Int. Cl.
*G06K 9/00*     (2006.01)
*C12N 5/075*     (2010.01)
(Continued)

(52) U.S. Cl.
CPC ........ *G06K 9/00134* (2013.01); *A61B 17/435* (2013.01); *C12N 5/0609* (2013.01);
(Continued)

(58) Field of Classification Search
CPC .................. G06K 9/00134; G06K 9/0014
See application file for complete search history.

(56) References Cited

U.S. PATENT DOCUMENTS

| 5,541,081 | A | * | 7/1996 | Hardy | ............. | G01N 33/5091 |
|---|---|---|---|---|---|---|
| | | | | | | 435/25 |
| 7,049,480 | B1 | * | 5/2006 | Christmann | ....... | A01K 67/0273 |
| | | | | | | 435/325 |

(Continued)

FOREIGN PATENT DOCUMENTS

| JP | 2010004789 A | 1/2010 |
|---|---|---|
| WO | 95/25810 A1 | 9/1995 |

(Continued)

OTHER PUBLICATIONS

Botros et al., "Metabolomics and its application for non-invasive embryo assessment in IVF", Molecular Human Reproduction 14(12):679-690 (2008).

(Continued)

*Primary Examiner* — Gandhi Thirugnanam
(74) *Attorney, Agent, or Firm* — Nixon Peabody LLP; David S. Resnick; Nicole D. Kling (57) ABSTRACT

The present invention generally relates to non-linear imaging systems and methods for use in various assisted reproductive technologies and other applications. In one aspect, the present invention is generally directed to two-photon and other non-linear microscope techniques that can be used to determine the status or maturity state of eggs or egg follicles, for example by determining the presence of polar bodies within the egg follicles. In some embodiments, endogenous (Continued)

metabolites, such as NADH or FAD, can be determined, and in some cases without externally altering those metabolite concentrations or without adding other compounds. Other embodiments of the invention are also directed to computer programs or systems that can be used to determine the status or maturity state of eggs or egg follicles, kits in such systems, or the like.

19 Claims, 4 Drawing Sheets

(51) Int. Cl.
  *G01N 33/50* (2006.01)
  *A61B 17/435* (2006.01)
  *G06T 5/20* (2006.01)
  *G06T 7/00* (2017.01)
(52) U.S. Cl.
  CPC ....... *G01N 33/5091* (2013.01); *G06K 9/0014* (2013.01); *G06T 5/20* (2013.01); *G06T 7/0012* (2013.01); *G06T 2207/10056* (2013.01); *G06T 2207/30024* (2013.01)

(56) References Cited

U.S. PATENT DOCUMENTS

| | | | | |
|---|---|---|---|---|
| 7,698,000 | B2* | 4/2010 | Silberberg | G02B 21/06 356/73 |
| 7,907,769 | B2* | 3/2011 | Sammak | G06K 9/00127 382/133 |
| 8,489,337 | B2* | 7/2013 | Hyde | A61K 35/54 424/1.21 |
| 8,497,063 | B2* | 7/2013 | Schenk | A01K 67/027 422/73 |
| 2008/0240527 | A1* | 10/2008 | Keller | G06F 17/30259 382/128 |
| 2008/0247628 | A1* | 10/2008 | Ramsing | G06K 9/00127 382/133 |
| 2009/0163764 | A1* | 6/2009 | Sher | C12Q 1/6881 600/34 |
| 2009/0184259 | A1* | 7/2009 | Ma | A61B 5/0059 250/483.1 |
| 2010/0195877 | A1* | 8/2010 | Oonishi | G06K 9/00147 382/128 |
| 2012/0142069 | A1* | 6/2012 | Shea | C12N 5/0012 435/178 |
| 2012/0276578 | A1* | 11/2012 | Stringari | G01N 21/6408 435/34 |
| 2017/0039415 | A1* | 2/2017 | Needleman | G06K 9/00134 |

FOREIGN PATENT DOCUMENTS

| | | |
|---|---|---|
| WO | 2007/080443 A3 | 7/2007 |
| WO | 2013/006948 A1 | 1/2013 |
| WO | 2014/110008 A1 | 7/2014 |

OTHER PUBLICATIONS

Buryakina et al., "Monitoring cellular metabolism of 3T3 upon wild type *E. coli* infection by mapping NADH with FLIM", Chinese Optics Letters 8(10):931-933 (2010).

Fernandes et al., "NLRP5 Mediates Mitochondrial Function in Mouse Oocytes and Embryos", Biology of Reproduction 8(5):138, 1-10 (2012).

Gadella et al., "Fluorescence lifetime imaging microscopy (FLIM): Spatial resolution of microstructures on the nanosecond time scale", Biophysical Chemistry 48:221-239 (1993).

Gardner et al., (Eds.) "Human Gametes and Preimplantation Embryos", Chapters 20, 21, and 23, Springer Science and Business Media New York (2013).

Ghukasyan et al., "Monitoring Cellular Metabolism with Fluorescence Lifetime of Reduced Nicotinamide Adenine Dinucleotide", J. Phys. Chem. 113:11532-11540 (2009).

Heikal, "Intracellulr coenzymes as natural biomarkers for metabolic activities and mitochondrial anomalies", Biomark Med. 4(2):241-263 (2010).

Hsieh et al., "Higher harmonic generation microscopy of in vitro cultured mammal oocytes and embryos", Optics Express 16(15):11574-11588 (2008).

Jasensky et al., "Peering Beneath the Surface: Novel Imaging Techniques to Noninvasively Select Gametes and Embryos for Art", Biology of Reproduction 89(4):105, 1-12 (2013).

Kyvelidou et al., "Qualification and Quantification of Pre-Implantation Embryo Health", Chapter 4 in Advances in Medicine and Biology 65:73-99 (2013).

Mayevsky et al., "Mitochondrial fucntion in vivo evaluated by NADH fluorescence: from animal models to human studies", Am J Physiol Cell Physiol. 292:C615-C640 (2007).

Quinn et al., "The Relationships Between the ATP Content of Preimplantation Mouse Embryos and Their Development in Vitro During Culture", J. Reprod. Fed. 35(2):301-309 (1973).

Skala et al., "In vivo microscopy of NADH and FAD redox states, fluorescence lifetimes, and cellular morphology in precancerous epithelia", PNAS 104(49):19494-19499 (2007).

Vergouw et al., "Day 3 embryo selection by metabolomic profiling of culture medium with near-infrafred spectroscopy as an adjunct to morphology: a randomized controlled trial", Human Reproduction 27(8):2304-2311 (2012).

\* cited by examiner

NON-LINEAR IMAGING SYSTEMS AND METHODS FOR ASSISTED REPRODUCTIVE TECHNOLOGIES

CROSS-REFERENCE TO RELATED APPLICATION

This application is a 35 U.S.C. § 371 National Phase Entry Application of International Application No. PCT/US2015/026123 filed Apr. 16, 2015, which designates the U.S. and claims benefit under 35 U.S.C. § 119(e) of U.S. Provisional Application No. 61/980,508 filed Apr. 16, 2014, the contents of which are incorporated herein by reference in their entirety.

FIELD

The present invention generally relates to non-linear imaging systems and methods for use in various assisted reproductive technologies and other applications.

BACKGROUND

Assisted Reproductive Technology (ART) has revolutionized treatment of human infertility in the past 30 years and has become standard practice in the U.S., where it accounts for over 1% of births. There are approximately 400 ART clinics in the U.S., which perform ~150,000 cycles per year (~900,000 cycles are performed worldwide per year), driving a multibillion dollar market. Despite wide spread use of ART, treatment is expensive and success rates are low: A cycle typically costs $10,000-$20,000 and only 10%-35% of cycles result in successful births. Patients are often tempted to have multiple embryos transferred in a single cycle to improve the odds of productive pregnancy, but this practice gives rise to high rates of multiple gestations. Multiple gestations greatly increase mortality rates and suffering for both infant and mothers, and produce substantial emotional and financial costs. Complications from multiple pregnancies from ART account for an estimated $1 billion of health care cost annually in the U.S. Therefore, there is a great need for technology which can increase the success rate and reduce the cost of ART.

In a typical ART treatment cycle, eggs are first retrieved from the patient and fertilized in vitro. One to three embryos are selected to transfer back to the patient, while the rest are frozen. If the patient becomes pregnant and gives birth to a healthy child, then the process is complete. If the pregnancy is unsuccessful, then the frozen embryos can be retrieved and transferred back to the patient, for another attempt at pregnancy.

One major reason for the low success rate of ART is the variable quality of eggs. Many factors contribute to egg quality in a manner that remains poorly understood, but it is known that only a subset of eggs collected from patients are at an appropriate stage of maturation. The fraction of immature eggs varies between patient populations and has not been well quantified, but values around 30% have been reported.

There has been substantial effort in both academia and industry to develop improved methods to measure egg and embryo quality, which would enable the healthiest embryos to be selected for implantation. The current method of predicting embryo quality is to examine embryo morphology prior to transfer using transmitted light microscopy systems, but that selection criterion is subjective and only produces the ~10%-35% success rate quoted above. Other methods being developed to determine egg and embryo quality include genomic, transcriptomic or proteomic assays, which require a biopsy of the embryo, and are thus highly invasive and severely reduce embryo survival rates. An alternative approach is to assay the metabolic state of the embryo by doing experiments to measure changes in metabolites in the embryo culture media, but this is indirect and has proven challenging, and can adversely affect the embryo due to the need to change metabolite levels. So far, none of these alternative methods have been clinically proven to be more successful than the traditionally used approach of examining embryo morphology with transmitted light microscopy.

SUMMARY

The present invention generally relates to non-linear imaging systems and methods for use in various assisted reproductive technologies and other applications. Specifically, the inventors have surprisingly discovered that non-linear imaging can be used to see the polar body in an egg cell. The inventors thus provide a novel imaging tool to see the polar body of an egg even when it is beneath the cumulus cells. The system can be used with or without image processing. Embryologists have no way today to see the polar body beneath the cumulus cells. The present technology thus offers significant benefit to the field of embryology providing new tools to assess the health and viability of an egg for, e.g., in vitro fertilization purposes. The systems providing image analysis are useful because identification of a polar body and its size/shape can be used for automation/reproducibility and a connection to viability. However, use of such image analysis is not necessary to use the system as described herein for identification of a polar body. The subject matter of the present invention involves, in some cases, interrelated products, alternative solutions to a particular problem, and/or a plurality of different uses of one or more systems and/or articles.

In one aspect, the present invention is generally directed to a method. In one set of embodiments, the method comprises acts of exposing an egg follicle to a non-linear microscope and acquiring a non-linear microscope image of the egg follicle to identify a polar body. The method can further comprise the step of determining a polar body, manually or automatically, within the image of the egg follicle.

The method can further comprise acts of acquiring a non-linear microscope image of at least two, three or a plurality of egg follicles, determining polar bodies within the images of the egg follicles, and separating the egg follicles based on the determination of the presence or absence of the polar bodies.

In another aspect, the present invention is generally directed to an apparatus, such as an apparatus for determining polar bodies. In accordance with one set of embodiments, the apparatus comprises a non-linear microscope, and a computer able to acquire an image from the non-linear microscope. The computer may further comprise a program that is able to determine a polar body within an egg follicle.

In yet another aspect, the present invention encompasses methods of making one or more of the embodiments described herein. In still another aspect, the present invention encompasses methods of using one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 2A-2J are images demonstrating image analysis performed for identifying a polar body in an egg follicle.

DETAILED DESCRIPTION

The present invention generally relates to non-linear imaging systems and methods for use in various assisted reproductive technologies and other applications. In one aspect, the present invention is generally directed to two-photon or other non-linear microscope techniques that can be used to determine the status or maturity state of eggs or egg follicles, for example by determining polar bodies within the egg follicles. In some embodiments, endogenous metabolites, such as NADH (nicotinamide adenine dinucleotide with hydrogen) or FAD (flavin adenine dinucleotide), can be determined, and in some cases without externally altering those metabolite concentrations or without adding other compounds. Other embodiments of the invention are also directed to computer programs or systems that can be used to determine the status or maturity state of eggs or egg follicles, kits involving such systems, or the like.

In one aspect, the present invention is generally directed to systems and methods for acquiring one or more non-linear microscope images of an egg follicle, e.g., to determine the status or maturity state of eggs and egg follicles in humans or other mammals. In general, non-linear microscope techniques include systems such as two-photon, three-photon, or multiphoton microscopy, second harmonic generation, third harmonic generation, and the like. In such techniques, to excite a fluorophore to emit a photon, two or more photons of light are often absorbed, unlike conventional (linear) microscopy where a single excitation photon interacts with a fluorophore to produce a single photon that is emitted. A variety of non-linear microscopes for two-photon and other non-linear microscope imaging may be obtained commercially.

The term non-linear microscopy refers to a general term that embraces any microscopy technique based on nonlinear optics (see, e.g., J. Mertz, Curr Opin Neurobiol. 2004 October; 14(5):610-6). Such techniques include, but are not limited to two-photon microscopy, three-photon microscopy, multiphoton microscopy, second harmonic generation, third harmonic generation, and high harmonic generation. In some aspects of all the embodiments, the methods and systems of the invention use two photon microscopy.

Using non-linear microscopy techniques such as discussed herein, egg follicles may be studied noninvasively, and often without the application of chemicals or other conditions that could alter the metabolic state of the eggs. In some embodiments, egg follicles are removed from a subject, such as a human subject, and are studied, in vitro, to identify those egg follicles containing a suitable mature egg and those egg follicles which do not. In some cases, the egg follicles may be separated based on the maturity state of the egg. For instance, one or more mature eggs may be selected for in vitro fertilization, implantation into a recipient, cryopreservation, etc., while immature eggs may be cryopreserved, allowed to mature further (e.g., upon exposure to suitable conditions), or the like.

The egg follicle typically comprises the egg and other cells, such as cumulus cells, granulosa cells, polar bodies, and the like. An egg (or oocyte) generally is the female germ cell. The cumulus cells surround and nourish the egg. These cells surround the fully-grown oocyte to form a cumulus-oocyte complex. Examples of cumulus cells include cumulus oophorus cells, cumulus granulosa cells, cumulus oophorous granulosa cells, granulosacumulus cells, etc. Cumulus cells may provide products for the acquisition of developmental competence, and/or vary in their hormonal responses and growth factors they produce. The absence of cumulus cells or insufficient numbers of cumulus cells usually impairs embryo production. Cumulus cells are required for the successful maturation of oocytes. Denuded oocytes in culture cannot undergo normal fertilization with standard insemination. Cumulus cells can synthesize an abundant muco-elastic extracellular matrix, which promotes oocyte extrusion from the egg follicle, a 20-40 fold increase in the volume of the cumulus mass. They likely also function as a selective barrier for sperm. Cumulus cells also show high expression of many enzymes of the glycolytic pathway and also neutral amino acid transporters. For example, their expression may be promoted by paracrine factors secreted by oocytes, which themselves do not readily take up L-alanine, and poorly metabolize glucose for energy production, and thus may depend on cumulus cells for their provision.

The systems and methods described herein permit one to visualize the polar body of an egg beneath the cumulus cells, and provide a novel way to visualize polar body in an intact isolated follicle wherein the egg is surrounded by other cells and wherein the egg was previously unaccessible for detailed viewing. Generally, an egg has one polar body. In some cases, an egg can have more than one polar body.

Figure 1A:
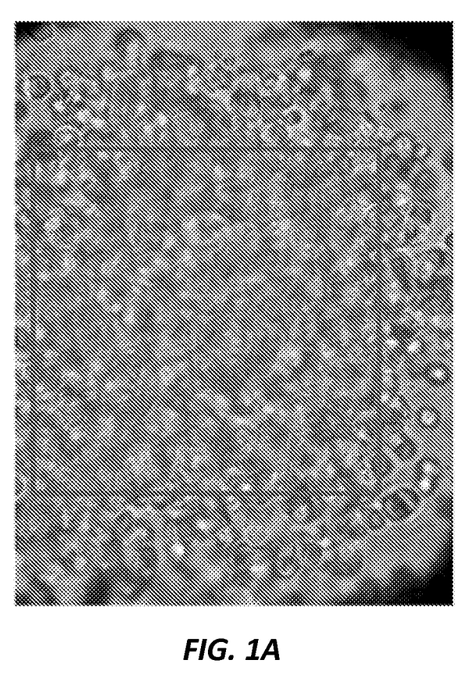
FIGS. 1A-1B illustrate the same field of view using conventional and two-photon microscopy, in accordance with one embodiment of the invention.
Figure 1B:
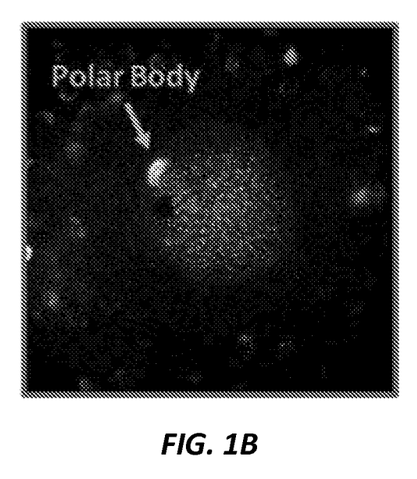

In some embodiments, the state of maturity of the egg follicle may be determined by determining polar bodies within the egg follicle using a non-linear microscopy technique, such as two-photon microscopy. For example, as is shown in FIG. 1B, a polar body may be readily determined using two-photon microscopy, while in the same field of view under conventional microscopy as is shown in FIG. 1A, it is difficult or impossible to determine or identify the polar body. One or more than one image may be taken of a sample, e.g., containing an egg follicle; for example, at least two or three or a plurality of images may be taken of a sample, and subsequently averaged. In some cases, more than one type of image may be taken of a sample. For instance, a sample may be studied using both two-photon microscopy and conventional microscopy, with images of the sample taken under both conditions.

Without wishing to be bound by any theory, it is believed that egg follicles containing suitably mature eggs also may contain polar bodies that can be determined using two-photon or other non-linear microscope techniques as discussed herein. In some embodiments, an egg is determined to be mature when the egg is identified to have a polar body. Polar bodies are generally created during meiotic division of a primary oocyte to form an egg, typically resulting in the formation of 3 polar bodies in addition to the egg itself. Such polar bodies typically undergo apoptosis or cell death after some time. Thus, it is believed that egg follicles containing suitably mature eggs will have well-developed polar bodies, while eggs that are immature may not have well-developed polar bodies, and egg follicles with eggs that have passed suitable maturity may have dying or dead polar bodies. In this way, in certain embodiments, it is believed that by determining the status of the polar bodies within an egg follicle, the maturity of the egg may also be determined.

As mentioned, in some embodiments, the state of maturity of an egg follicle may be determined by determining the status of polar bodies within the egg follicles, e.g., using various non-linear microscopy techniques, such as two-photon microscopy. Without wishing to be bound by any theory, it is believed that eggs and polar bodies often can have relatively large concentrations of certain endogenous fluorophores, which can be determined to determine the eggs and polar bodies. For example, polar bodies may contain relatively large amounts of endogeneous NADH (nicotinamide adenine dinucleotide with hydrogen) or FAD (flavin adenine dinucleotide), even compared to the egg. Thus, using two-photon or other non-linear microscope techniques such as those discussed herein, the presence and/or concentrations of NADH or FAD within the egg follicle may be determined, e.g., to identify polar bodies. NADH and FAD can exhibit fluorescence, and are endogenously present in many cells. In addition, NADH and FAD are both involved in cellular metabolism. Accordingly, in some embodiments, by determining the concentrations of NADH or FAD within an egg follicle, using non-linear microscopy techniques such as two-photon microscopy or other techniques as discussed herein, the maturity of the egg may be determined by determining polar bodies. While in some cases, the determination of fluorophores such as NADH and/or FAD may be relatively quantitative (e.g., such that the concentrations of NADH and/or FAD may be determined), in other cases, the determination of the fluorophores is mainly qualitative, e.g., such that morphology of the cells within the egg follicle can be determined.

A fluorophore which is excited by a photon will drop to the ground state with a certain probability based on the decay rates through a number of different (radiative and/or nonradiative) decay pathways. To observe fluorescence, one of these pathways may be by spontaneous emission of a photon. This can be utilized for making non-intensity based measurements in chemical sensing. While in some embodiments, fluorophores can be added to facilitate determination of the polar bodies, in other embodiments, no external fluorophores are needed, and endogenously-present fluorophores, such as NADH or FAD, may be determined, e.g., using two-photon, three-photon, or multiphoton microscopy or other non-linear microscopy techniques. In addition, it should be understood that the exact identity of the fluorophores that are imaged need not necessarily be determined in certain embodiments. Other endogenous fluorophores within the polar bodies may be imaged, in addition to or instead of NADH and/or FAD, for example, flavins, retinol, tryptophan, derivatives indoleamine, etc. Thus, as mentioned, the fluorophores may be used to determine cellular morphology in some cases, e.g., of a polar body, rather than to determine specific fluorophores within the cell.

In some aspects of all the embodiments, the direct autofluorescence of NADH can be analyzed using a wavelength of about 740 nm in two-photon fluorescence excitation and using an emission bandpass filter centered around about 460 nm. In some aspects of all the embodiments, the direct autofluorescence of NADH can also be analyzed using a wavelength of about 370 nm in fluorescence excitation and using an emission bandpass filter centered around about 460 nm. In some aspects of all the embodiments, the direct autofluosescence of FAD can be analyzed using a wavelength of about 900 nm in two-photon fluorescence excitation and using an emission bandpass filter centered around about 550 nm. The direct autofluorescence of FAD can also be analyzed in some embodiments using a wavelength of about 450 nm in one-photon fluorescence excitation and using an emission bandpass filter centered around about 550 nm. In some cases, the NADH and FAD may be determined simultaneously and/or sequentially.

In addition, in certain aspects of all the embodiments, two-photon images may be obtained using excitation light having a wavelength of between about 700 nm and about 1200 nm, between 750 nm and about 1150 nm, or between about 800 nm and about 1000 nm. In some cases, the emission light may have a wavelength of between about 500 nm and about 800 nm, between 550 and about 750 nm, or between about 600 nm and about 700 nm.

The concentration of NADH or FAD can be determined based on the nonlinear microscopy images using methods such as those disclosed in, e.g., Yu et al., Journal of Photochemistry and Photobiology B: Biology 95 (2009) 46-57.

In some embodiments, only a single image is obtained, e.g., based on two-photon (or other non-linear) imaging of NADH, FAD, and/or other suitable metabolites or fluorophores present within the egg follicle, e.g., endogenously. The single image is taken at one Z dimension. As used herein, the term "Z dimension" refers to the dimension that is perpendicular to the focal plane of the microscope system. Surprisingly, the polar body can be readily determined under suitable conditions, even when the polar body is surrounded by other cells, by using two-photon or other non-linear imaging techniques as discussed herein. In contrast, conventional microscopy techniques often cannot penetrate the egg follicle to determine the condition of cells within it. However, it should be understood that in some aspects of all the embodiments, more than one such image may be obtained and/or more than one microscopy technique may be used for imaging, e.g., to produce multiple images.

In some cases, one or more images (e.g., 2, 3, 4, 5, 6, 7, 8, 9, or more) may be acquired relatively rapidly, and in some cases, non-invasively or minimally invasively. The two ore more images can be taken at at least two or three or a plurality of Z dimensions. A step motor-connected to a computer can permit the movement of the sample or the microscope objective lens for the purpose of taking a plurality of non-linear microscope images at at least two or three or a plurality of Z dimensions. In some cases, the analysis may take a relatively short amount of time, such as 30 seconds to 5 minutes. In some cases, the analysis may be multiplexed and automated. The imaging time may vary and may be set for any intervals. Typically, for example, it takes about 1-5 minutes, 1-2 min, 1-3 min, 1-4 min or sometimes 30 seconds to 2 minutes, 40 seconds to 1-2 minutes, 45 seconds to 1-2 minutes to load a sample containing the cells to be studied, and only seconds to acquire the images. Thus, in some cases, an egg follicle may be studied or imaged in less than about 10 minutes, less than about 5 minutes, less than about 3 minutes, less than about 2 minutes, less than about a minute. In some cases, the images may also be studied, e.g., using a computer to identify polar bodies or the like, after which the sample that has been analyzed can either be selected for further fertilization or implantation, discarded as not optimally fit for these procedures, or the like, e.g., as discussed herein. More than one Z dimension images will allow various viewpoints of the egg to image and locate the polar body.

In some aspects of all the embodiments, the two or more images comprise a fluorescence image of NADH and a fluorescence image of FAD.

In some aspects of all the embodiments, the polar body can be determined by visual inspection of the non-linear microscope image.

Figure 2A:
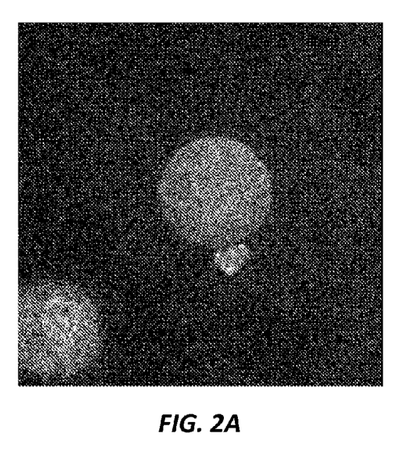
(FIG. 2A) A two-photon microscopy image.

In some aspects of all the embodiments, the polar body can be determined by computerized image analysis. The image analysis can be either automated or manual. The image analysis comprises a step of performing a first image analysis on the non-linear microscope image to identify an egg inside the egg follicle. The first image analysis comprises (a) applying a first bandpass filter to the non-linear microscope image such as shown in FIG. 2A to eliminate noise and (b) performing a first algorithm to identify the boundary of the egg. The first bandpass filter can substantially eliminate frequencies above and below a predetermined value or range of values. It is known in the art that bandpass filtering in image process comprises one or more Fourier transforms. The Fourier transform is a mathematical operation that transforms the original measure or signal into an expression of complex exponentials with a range of amplitude coefficients and frequency terms. An image, being a two dimensional array of intensity measurements, can also be transformed to two dimensional arrays of complex exponentials. This Fourier transformation is often referred to as a transformation from the spatial domain to the frequency domain. In the frequency domain, one can highlight specific structures and remove others for subsequent analysis by removing certain frequencies from the transform and then calculating the inverse transform. An example of a first processed image after the application of the first bandpass filter can be seen in FIG. 2B.

Figure 2B:
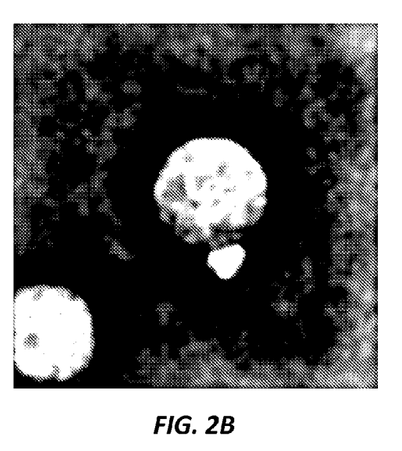
(FIG. 2B) A processed image after a bandpass filter is applied.
Figure 2C:
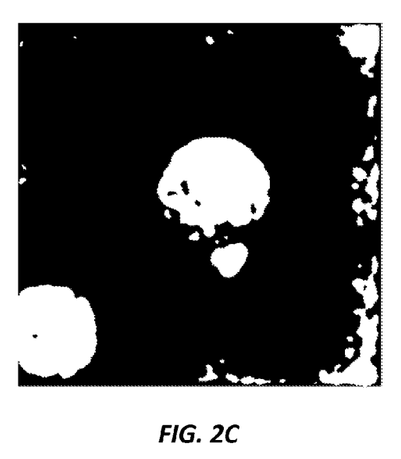
(FIG. 2C) A binary image after a threshold operation is performed.

In some aspects of all the embodiments, the first image analysis further comprises performing image thresholding on the first processed image, which converts the first processed image to a binary image, such as shown in FIG. 2C. The binary image is a second processed image. A binary image is a digital image that has only two possible values for each pixel. Typically the two colors used for a binary image are black and white though any two colors can be used. The threshold value used in the image thresholding can be determined by Otsu's method.

Figure 2D:
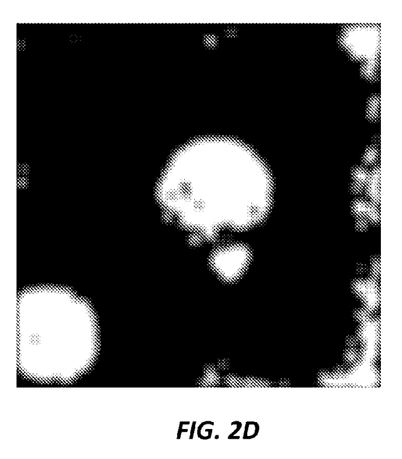
(FIG. 2D) A processed image after a Gaussian blur is performed.
Figure 2E:
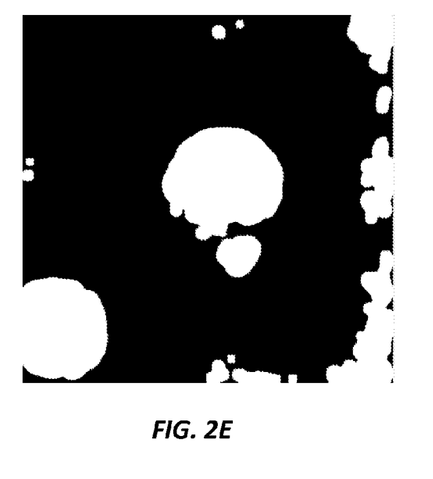
(FIG. 2E) A processed image after another bandpass filter is applied.

In some aspects of all the embodiments, the first image analysis further comprises performing a Gaussian blur on the second processed image. This can produce a third processed image such as shown in FIG. 2D. Gaussian blur is a widely used effect in graphics software. It is typically used to reduce image noise and reduce detail levels, so that the image appears smoother. The Gaussian blur can connect segments of large blobs in the second processed image. In some embodiments, the first image analysis can further comprise another step of image thresholding on the third processed image to further remove noise such as shown in FIG. 2E.

In some aspects of all the embodiments, the first image analysis further comprises identifying isolated pixel clusters, e.g., by using number of neighbors. A step of iterative erosion can be performed on each cluster to separate connected clusters. Clusters that are outside of a predetermined area range can be eliminated. For example, the predetermined area range can be 5000 pixels to 100000 pixels, 5000 pixels to 90000 pixels, 5000 pixels to 80000 pixels, 5000 pixels to 70000 pixels, 5000 pixels to 60000 pixels, 5000 pixels to 50000 pixels, or 10000 pixels to 50000 pixels.

Figure 2F:
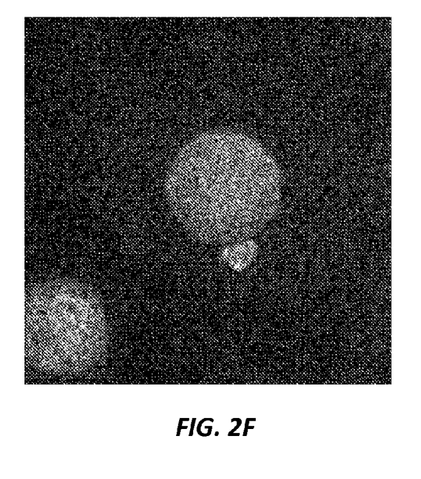
(FIG. 2F) The boundary of the egg is superimposed on the two-photo microscopy image shown in FIG. 2A.

In some aspects of all the embodiments, the first algorithm comprises performing an active contour algorithm to identify the boundary of the egg. The use of active contour model to delineate an object outline from a possibly noisy 2D image is known in the art. The identified boundary can be superimposed on the non-linear microscope image such as shown in FIG. 2F.

Figure 2G:
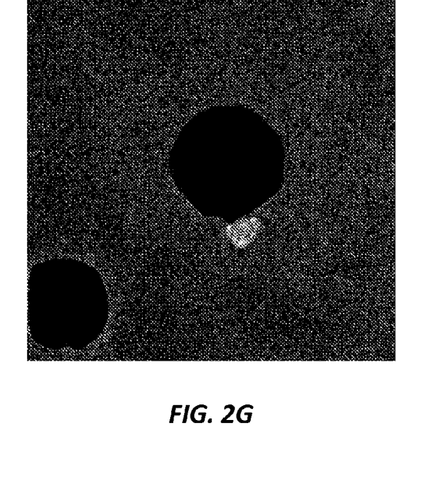
(FIG. 2G) A processed image where the pixels of the identified egg are removed.

After the boundary of the egg is identified, the image analysis further comprises performing a second image analysis on the non-linear microscope image to identify the polar body, wherein the second image analysis comprises (c) optionally removing pixels that represent the identified egg from the non-linear microscope image (e.g., see FIG. 2G); (d) applying a second bandpass filter to the image to eliminate noise; and (e) performing a second algorithm to identify the boundary of the polar body.

In some aspects of all the embodiments, the second image analysis comprises identifying a polar body candidate in the image and determining the characteristics of the polar body candidate. Examples of the characteristics of the polar body include, but are not limited to, area, brightness, and circularity. Circularity is a dimensionless number, and can be calculated as perimeter$^2$/(4*pi*Area). Circularity can also be calculated as 1 minus the ratio of the eigenvalues of the moment of inertia tensor. The characteristics of the polar body candidate can be used to determine whether the candidate is a real polar body. A combination of the characteristics can be used for the determination. The actual threshold value for a particular characteristic used for the determination depends on the imaging conditions such as the pixel size.

In some aspects of all the embodiments, the polar body candidate is a polar body when the circularity of the candidate is no more than 0.2. In some embodiments, the polar body candidate is a polar body when the circularity of the candidate is no more than 0.15. In some embodiments, the polar body candidate is a polar body when the circularity of the candidate is no more than 0.1. In some embodiments, the polar body candidate is a polar body when the circularity of the candidate is no more than 0.05.

In some aspects of all the embodiments, the polar body candidate is a polar body when the area of the candidate is between 500 and 10,000 pixels. In some embodiments, the polar body candidate is a polar body when the area of the candidate is between 500 and 8,000 pixels. In some embodiments, the polar body candidate is a polar body when the area of the candidate is between 500 and 6,000 pixels. In some embodiments, the polar body candidate is a polar body when the area of the candidate is between 1,000 and 8,000 pixels. In some embodiments, the polar body candidate is a polar body when the area of the candidate is between 1,000 and 6,000 pixels.

The image analysis described herein can be performed using existing software such as MATLAB, Mathematica, and ImageJ. The image analysis described herein can also be performed using customized script.

In some aspects of all the embodiments, an egg identified to have a polar body is selected for in vitro fertilization or cryopreservation. In some aspects of all the embodiments, the egg identified and selected for in vitro fertilization or cryopreservation is further in vitro fertilized or cryopreserved.

In addition, it should be noted that, in some aspects of all the embodiments, such microscope techniques can be used in the absence of any calibration of metabolite concentrations, or exposure of the egg follicle to conditions which alter metabolite concentrations within the egg follicle, unlike many prior art techniques, for example, where the egg follicle is exposed to conditions which reduce endogenous NADH or other metabolite concentrations. For instance, in some prior art techniques, to obtain information about the metabolic state of an oocyte using NADH, one must first reduce the endogenous NADH concentration of the oocyte by placing it in a control medium and obtaining at least one control NADH fluorescence measurement. After the control measurement, the oocyte is subjected to a different medium with a nutrient for a time period and the change in the NADH concentration was observed within the oocyte. This analysis is not only time-consuming, but also subjects the oocyte to an additional and unnecessary stress when it is moved from special medium to another.

However, surprisingly, using various non-linear microscopy techniques such as two-photon microscopy, the need for exposing egg follicles to such conditions can be avoided altogether, thereby minimizing stresses placed on the egg follicles during their analysis, according to various embodiments. Thus, as discussed herein, NADH and/or FAD may be determined within an egg follicle in certain embodiments without subjecting the egg follicle to changes in its culture medium. Accordingly, the egg follicles are not exposed to various media to assess the metabolic state of the egg follicle (e.g., by altering levels of NADH or FAD within the egg follicle), or the egg follicles may be exposed to conditions which maintain NADH (or other metabolite) concentrations near endogenous NADH concentrations (e.g., between about 80% and about 120%, between about 90% and about 110%, between about 95% and about 105%, etc.), according to certain embodiments. Thus, in some cases, the egg follicle may be determined without subjecting it to changes in its culture medium.

In various embodiments, non-linear microscope images of an egg follicle are acquired using a suitable microscope. For example, in one embodiment, the microscope can be a self-contained, microscope setting, such as a box, such as a table-top microscope box that is typically used at in vitro fertilization clinics to select oocytes for fertilization and embryos for transfer. The egg follicles may be placed within the microscope for study, for example, in a well suitable for imaging and comprising cell culture medium at 37° C. Such microscopes can be used with egg follicles, oocytes, embryos, etc. as well as cumulus cells and cells isolated from an embryo that can be acquired by any procedure and placed in any media. Thus the devices and methods described herein can be compatible with the current practices in in vitro fertilization clinics and other settings where assessment of embryos or oocytes is performed.

In addition, in some cases, a computer may be used to acquire non-linear microscope images of the egg follicle, and/or to determine polar bodies within the egg follicle, e.g., the location, status, condition, shape, etc. of the polar bodies. For example, two-photon images as discussed above may be analyzed using a computer to determine whether polar bodies are present or not, and/or to determine the condition, age, size, etc. of the polar bodies, e.g., using conditions such as those described herein. The computer may be any suitable computer, e.g., a general-purpose computer or a specially-built computer, etc.

In addition, in some embodiments, techniques such as these can be combined with FLIM (fluorescence lifetime imaging microscopy) or other techniques that can determine decay rates of fluorophores from a fluorescent sample. In such techniques, fluorescence lifetime histograms of the fluorophores may be determined, e.g., using a pulsed light source to acquire multiple images of a sample. Examples of FLIM techniques are discussed in International Patent Application No. PCT/US14/10435, filed Jan. 7, 2014, entitled "Metabolic Imaging Methods for Assessment of Oocytes and Embryos," incorporated herein by reference in its entirety.

The egg follicles may be analyzed in any suitable cell culture medium used for analyzing embryos, oocytes, cumulus cells, embryos, etc., according to certain embodiments. Thus, the present methods, in certain embodiments, can be used to avoid subjecting the cells to any extraordinary medium changes. Moreover, because there is no need to change the metabolic state of the cell, no additional time is needed for the analysis, making the analysis fast and convenient according to some embodiments of the invention.

The egg follicle can be in or be placed in any normal cell culture medium used in maintaining the egg follicle. In some cases, the culture media may be selected to meet the metabolic needs of the egg follicle, e.g., by addressing amino acid and energy requirements based on the specific developmental stage of the egg follicle. Examples of various culture media include, but are not limited to, the following. Culture media, like Earle, Ham's F10, Tyrode's T6 and Whitten's WM1 are based on different salts and were constructed to support the development of somatic cells and cell lines in culture. These media may be formulated for use with or without serum supplementation, depending on the cell type being cultured. Ham's Nutrient Mixtures were originally developed to support growth of several clones of Chinese hamster ovary (CHO) cells, as well as clones of HeLa and mouse L-cells. Serum albumin may also be added in some cases as a source for amino acids. Albumin or synthetic serum may be added in concentrations of, for example, 5 to 20% (w/v or v/v, respectively). Serum proteins may be used to ensure that the egg follicles do not substantially adhere to the surfaces of pipettes or other devices used to manipulate them. One such example medium is entitled B2. Another example is a formula entitled Human Tubal Fluid (HTF), which mimics the in vivo environment. The formulation of HTF was based on the chemical composition of the fluids in human fallopian tubes as known at that time. This medium is based on a simple balanced salt solution without amino acids; however, the concentration of potassium was adjusted to that measured in the human female reproductive tract.

Still other examples are two culture media G1 and G2 that are to be used in sequence. G1 supports the in vitro development of the fertilized oocyte, the zygote, to the 8-cell stage, and G2 from 8 cells to blastocyst. Several modifications to these media also exist and are well known to one skilled in the art. Another non-limiting example includes culture media containing a phosphate buffer or Hepes organic buffer. The pH and osmolality may utilize a bicarbonate/$CO_2$ buffer system to keep pH in the range of 7.2-7.4. The osmolarity of the culture medium may be in the range of 275-290 mosmol/kg. As another example, the medium may be commercial IVF media. Commercial IVF media typically comprises, for example, one or more of the following components: synthetic serum, recombinant albumin, salt solution in MTF, NaCl, KCl, $KH_2PO_4$, $CaCl_2$, $MgSO_4$, $NaHCO_3$, and carbohydrates. Carbohydrates are present in the female reproductive tract. Their concentrations vary throughout the length of the oviduct and in the uterus, and are also dependent on the time of the cycle. In some cases, the media may be further supplemented with non-essential amino acids, such as proline, serine, alanine, aspargine, aspartate, glycine, and/or glutamate. In some cases, the media may be further supplemented with essential amino acids, such as cystine, histadine, isolucine, leucine, lysine, methionine, valine, argentine, glutamine, phenylalanine, therionine, and/or tryptophan. The egg follicles may, in some cases, be cultured or studied under paraffin oil, which prevents evaporation of the medium preserving a constant osmolarity. The oil also may be used to minimize fluctuations of pH and temperature when the egg follicles are taken out of an incubator for microscopic assessment. In addition, the egg follicles may be kept in a temperature-sensitive and a humidified incubator with a temperature setting of 37.0-37.5° C. Similar temperatures may be maintained while imaging the egg follicles.

One aspect of the invention relates to a method of monitoring embryo development, the method comprising: (i) loading a dish containing an embryo onto a loading platform of an imaging system capable of performing non-linear measurements; (ii) acquiring time-lapse non-linear microscope images of the embryo with the imaging system; and (iii) analyzing the time-lapse non-linear microscope images to determine the suitability of the embryo for in vitro fertilization. Time-lapse imaging may be performed with any computer-controlled microscope that is equipped for digital image storage and analysis, for example, inverted microscopes equipped with heated stages and incubation chambers, or custom built miniature microscope arrays that fit inside a conventional incubator.

Images that are acquired may be stored either on a continuous basis, as in live video, or on an intermittent basis, as in time lapse photography, where a subject is repeatedly imaged in a still picture. The time interval between images could be varied depending on the amount of cell activity.

International Patent Application No. PCT/US14/10435, filed Jan. 7, 2014, entitled "Metabolic Imaging Methods for Assessment of Oocytes and Embryos," is hereby incorporated by reference in its entirety.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

Although any known methods, devices, and materials may be used in the practice or testing of the invention, the methods, devices, and materials in this regard are described herein.

Some embodiments of the invention are listed in the following numbered paragraphs:

1. A method, comprising:
acquiring a non-linear microscope image of an egg follicle; and
determining a polar body within the image of the egg follicle.
2. The method of paragraph 1, wherein the non-linear microscope image is a two-photon microscope image.
3. The method of paragraph 1, wherein the non-linear microscope image is a multiphoton microscope image.
4. The method of paragraph 1, wherein the non-linear microscope image is a second harmonic generation microscope image.
5. The method of paragraph 1, wherein the non-linear microscope image is a third harmonic generation microscope image.
6. The method of any one of the paragraphs 1-5, wherein the non-linear microscope image is a fluorescence image of endogenous NADH inside the egg follicle.
7. The method of paragraph 6, wherein the egg follicle is exposed to conditions which maintain NADH concentrations within the egg follicle to between 80% and 120% of endogenous NADH concentrations.
8. The method of paragraph 6 or 7, wherein the egg follicle is exposed to conditions which do not alter the NADH concentrations within the egg follicle.
9. The method of any one of the paragraphs 1-5, wherein the non-linear microscope image is a fluorescence image of endogenous FAD inside the egg follicle.
10. The method of paragraph 9, wherein the egg follicle is exposed to conditions which maintain FAD concentrations within the egg follicle to between 80% and 120% of endogenous FAD concentrations.
11. The method of paragraph 9 or 10, wherein the egg follicle is exposed to conditions which do not alter the FAD concentrations within the egg follicle.
12. The method of any one of the paragraphs 1-11, wherein the polar body is determined by visual inspection.
13. The method of any one of the paragraphs 1-11, wherein the polar body is determined by computerized image analysis.
14. The method of any one of the paragraphs 1-13, further comprising determining that an egg is mature if the egg is identified to have the polar body.
15. The method of paragraph 14, further comprising a step of selecting the mature egg for in vitro fertilization.
16. The method of paragraph 14 or 15, further comprising a step of performing in vitro fertilization with the mature egg.
17. The method of any one of the paragraphs 1-16, wherein the egg follicle is beneath cumulus cells.
18. The method of any one of paragraphs 1-17, wherein the egg follicle is a human egg follicle.
19. An in vitro method of identifying a polar body in an isolated egg follicle, the method comprising:
(i) acquiring, with an imaging system, a non-linear microscope image of the egg follicle at one Z dimension, wherein the Z dimension is perpendicular to the focal plane of the microscope system;

(ii) performing a first image analysis on the non-linear microscope image to identify an egg inside the egg follicle, wherein the first image analysis comprises (a) applying a first bandpass filter to the non-linear microscope image to eliminate noise, thereby substantially eliminating frequencies above and below a predetermined value or range of values; and (b) performing a first algorithm to identify the boundary of the egg; and (iii) performing a second image analysis on the non-linear microscope image to identify the polar body, wherein the second image analysis comprises (c) removing pixels that represent the identified egg from the non-linear microscope image; (d) applying a second bandpass filter to the image to eliminate noise; and (e) performing a second algorithm to identify the boundary of the polar body.

20. The method of paragraph 19, wherein a plurality of polar bodies are identified for a plurality of eggs inside the egg follicle.

21. The method of paragraph 19 or 20, wherein the first image analysis comprises performing image thresholding, thereby converting the non-linear microscope image to a binary image.

22. The method of any one of the paragraphs 19-21, wherein the first image analysis further comprises performing a Gaussian blur.

23. The method of any one of the paragraphs 19-22, wherein the first image analysis further comprises identifying isolated pixel clusters and performing an iterative erosion on each cluster to separate connected clusters.

24. The method of any one of the paragraphs 19-23, wherein the first algorithm comprises an active contour algorithm.

25. The method of any one of the paragraphs 19-24, wherein the second image analysis further comprises identifying a polar body candidate in the image and determining the area, brightness, and/or circularity of the polar body candidate.

26. The method of paragraph 25, further comprising determining that the polar body candidate is a polar body as a function of any one of the area, brightness, circularity of the polar body candidate, and any combinations thereof.

27. The method of any one of the paragraphs 19-26, wherein the non-linear microscope image is a two-photon microscope image.

28. The method of any one of the paragraphs 19-26, wherein the non-linear microscope image is a multiphoton microscope image.

29. The method of any one of the paragraphs 19-26, wherein the non-linear microscope image is a second harmonic generation microscope image.

30. The method of any one of the paragraphs 19-26, wherein the non-linear microscope image is a third harmonic generation microscope image.

31. The method of any one of the paragraphs 19-30, wherein the non-linear microscope image is a fluorescence image of endogenous NADH inside the egg follicle.

32. The method of paragraph 31, wherein the egg follicle is exposed to conditions which maintain NADH concentration within the egg follicle to between 80% and 120% of the endogenous NADH concentration.

33. The method of paragraph 31 or 32, wherein the egg follicle is exposed to conditions which do not alter the NADH concentration within the egg follicle.

34. The method of any one of the paragraphs 19-30, wherein the non-linear microscope image is a fluorescence image of endogenous FAD inside the egg follicle.

35. The method of paragraph 34, wherein the egg follicle is exposed to conditions which maintain FAD concentration within the egg follicle to between 80% and 120% of the endogenous FAD concentration.

36. The method of paragraph 34 or 35, wherein the egg follicle is exposed to conditions which do not alter the FAD concentration within the egg follicle.

37. The method of any one of the paragraphs 19-36, further comprising a step of taking a plurality of non-linear microscope images of the egg follicle at a plurality of Z dimensions.

38. The method of any one of the paragraphs 19-37, wherein the first and second image analyses are automated.

39. The method of any one of the paragraphs 19-38, further comprising determining that an egg is mature if the egg is identified to have a polar body.

40. The method of paragraph 39, further comprising a step of selecting the mature egg for in vitro fertilization.

41. The method of paragraph 39 or 40, further comprising a step of performing in vitro fertilization with the mature egg.

42. The method of any one of the paragraphs 19-41, wherein the egg is a human egg.

43. A method of monitoring embryo development, the method comprising:

(i) loading a dish containing an embryo onto a loading platform of an imaging system capable of performing non-linear measurements;

(ii) acquiring time-lapse non-linear microscope images of the embryo with the imaging system; and (iii) analyzing the time-lapse non-linear microscope images to determine the suitability of the embryo for in vitro fertilization.

44. The method of paragraph 43, wherein the embryo is a human embryo.

45. The method of paragraph 43 or 44, further comprising displaying the time-lapse non-linear microscope images.

46. The method of any one of the paragraphs 43-45, wherein the imaging system is placed inside an incubator.

47. The method of any one of the paragraphs 43-46, wherein the method is automated.

48. The method of any one of the paragraphs 43-47, wherein the time-lapse non-linear microscope images are two-photon microscope images.

49. The method of any one of the paragraphs 43-47, wherein the time-lapse non-linear microscope images are multiphoton microscope images.

50. The method of any one of the paragraphs 43-47, wherein the time-lapse non-linear microscope images are second harmonic generation microscope images.

51. The method of any one of the paragraphs 43-47, wherein the time-lapse non-linear microscope images are third harmonic generation microscope images.

52. The method of any one of the paragraphs 43-51, wherein the time-lapse non-linear microscope images are fluorescence images of endogenous NADH inside the embryo.

53. The method of any one of the paragraphs 43-51, wherein the time-lapse non-linear microscope images are fluorescence images of endogenous FAD inside the embryo.

54. The method of any one of the paragraphs 43-51, wherein the time-lapse non-linear microscope images are a combination of fluorescence images of endogenous NADH inside the embryo and fluorescence images of endogenous FAD inside the embryo.

55. The method of in vitro fertilization comprising the steps of identifying a polar body in an egg follicle by a method of any one of the paragraphs 19-42 and fertilizing the egg having the polar body in vitro when the polar body is identified.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages may mean±1% of the value being referred to. For example, about 100 means from 99 to 101.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The following examples are intended to illustrate certain embodiments of the present invention, but do not exemplify the full scope of the invention.

Example 1

This example illustrates the analysis of an egg follicle and the determination of a polar body within the egg follicle, in accordance with one embodiment of the invention.

An egg follicle was obtained and prepared for analysis using two-photon microscopy. The excitation wavelength was 940 nm and the power was 30 mW. The emission (collected light) was observed with a 650 nm short pass filter. The microscope system was constructed around an inverted microscope (Eclipse Ti, Nikon), with a Ti:sapphire pulsed laser (Mai-Tai, Spectra-Physics) for excitation (80 MHz repetition rate, ~70 fs pulse width), a commercial scanning system (DCS-120, Becker & Hickl GmbH), and hybrid detectors (HPM-100-40, Becker & Hickl GmbH). An image of the egg follicle may be seen in FIG. 1B, with the polar body within the egg follicle identified.

Without wishing to be bound by any theory, it is believed that the presence of FAD is determined in this image, which identifies the polar body within the egg follicle. For comparison purposes, a conventional light microscopy image of the same region of the egg follicle is shown in FIG. 1A, showing that the egg follicle is substantially larger than the polar body, and that under conventional microscopy, it is difficult or impossible to identify either the egg or the polar body when these are surrounded by a variety of different cells, including cumulus cells.

Example 2

This example illustrates image analysis and the determination of a polar body within an egg follicle, in accordance with one embodiment of the invention.

Figure 2H:
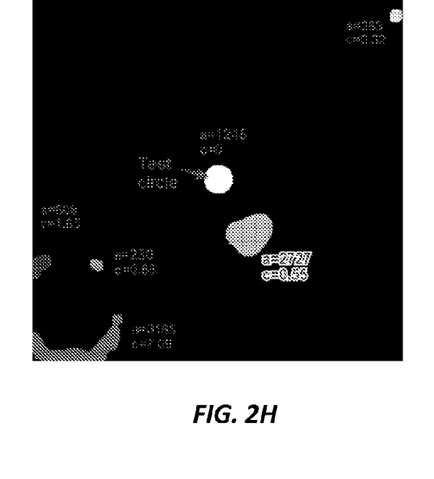
(FIG. 2H) A processed image showing a plurality of polar body candidates.

The following steps are performed to determine a polar body within an egg follicle (FIG. 2A) using the technology described herein:

(a) First find the eggs.
  (i) Run bandpass filter: Fourier transform, eliminate frequencies above and below bandpass values, then Fourier transform back (FIG. 2B).
  (ii) Perform a threshold operation to convert to a binary image (white or black pixels). Threshold value calculated using Otsu's method (FIG. 2C).
  (iii) Perform a Gaussian blur to connect segments of large blobs, then another threshold (FIGS. 2D-2E).
  (iv) Find isolated pixel clusters (using number of neighbors).
  (v) Perform an iterative erosion on each cluster to separate clusters that are connected, but shouldn't be (e.g., a polar body pixel cluster connected to egg). Eliminate clusters that are outside of an area range ([10000 pixels and 50000 pixels]).
  (vi) After these operations, the remaining clusters correspond to eggs.
  (vii) Use an active contour algorithm to tighten the mask to the boundary of the egg (FIG. 2F).
(b) Then find the polar body.
  (viii) Using the masks just obtained, remove these pixels representing the eggs from the original image to make it easier to find the polar body (FIG. 2G).
  (ix) Find smaller blobs (polar body candidates), use different bandpass values for a smaller object.
  (x) Filter blobs by area and circularity (FIG. 2H).

(xi) Find the closest egg to each blob.

(xii) Then go back for each egg and find the closest of the neighboring blobs that fall within the size and circularity filter values to determine the polar body.

(xiii) Use active contours again to tighten up the boundary.

Figure 2I:
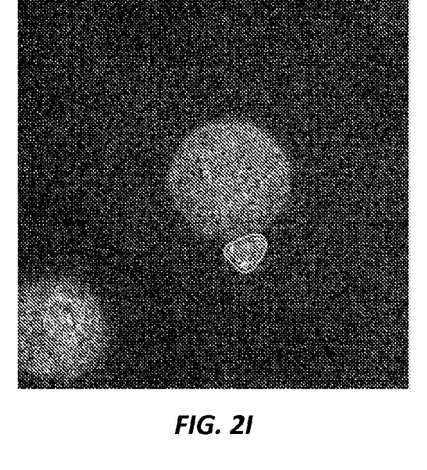
(FIG. 2I) The boundary of the polar body is superimposed on the image shown in FIG. 2F.

(xiv) The final result can be shown in FIG. 2I.

(c) Quantitative traits of the polar body can be calculated. Some of these traits (e.g., area, circularity, or average brightness) may correlate with viability.

Figure 2J:
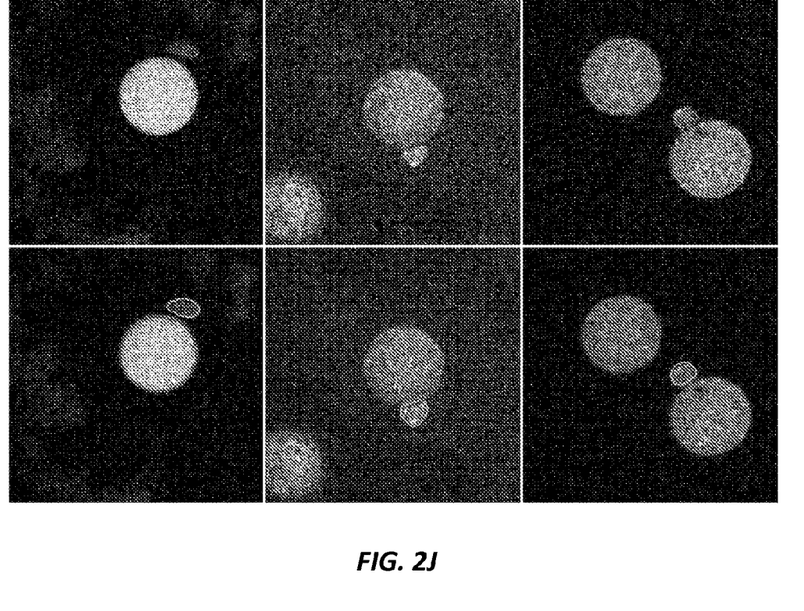
(FIG. 2J) A set of two-photon microscopy images showing that a plurality of eggs can be identified simultaneously.

Multiple eggs and/or polar bodies can be identified at the same time (FIG. 2J).

Example 3

This example illustrates the safety of the technology described herein on cells.

Two groups of mouse embryos were exposed to different levels of illumination, and one group of embryos was kept in the incubator as a control.

For the high exposure group, the following imaging conditions were used: Scan samples for 20 s at 750 nm (for NADH) with 10 mW and a numerical aperture of 1.25. Note, each egg only takes up about 1/10th of the area of the scan, so effectively it is receiving 1/10th the light dosage of that 20 seconds of scan. Samples were then scanned for another 20 s at 845 nm (for FAD) with a power of 20 mW.

Six days later, all of the embryos had hatched to blastocyst, so even the higher light dosage appears to be safe.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An in vitro method of identifying a polar body in an isolated egg follicle, the method comprising:
   (i) acquiring, with an imaging system, a non-linear microscope image of the egg follicle at one Z dimension, wherein the Z dimension is perpendicular to the focal plane of the microscope system;
   (ii) performing a first image analysis on the non-linear microscope image to identify an egg inside the egg follicle, wherein the first image analysis comprises (a) applying a first bandpass filter to the non-linear microscope image to eliminate noise, thereby substantially eliminating frequencies above and below a predetermined value or range of values; and (b) performing a first algorithm to identify the boundary of the egg; and
   (iii) performing a second image analysis on the non-linear microscope image to identify the polar body, wherein the second image analysis comprises (c) removing pixels that represent the identified egg from the non-linear microscope image; (d) applying a second bandpass filter to the image to eliminate noise; and
   (e) performing a second algorithm to identify the boundary of the polar body.

2. The method of claim 1, wherein a plurality of polar bodies are identified for a plurality of eggs inside the egg follicle.

3. The method of claim 1, wherein the first image analysis comprises performing image thresholding, thereby converting the non-linear microscope image to a binary image.

4. The method of claim 1, wherein the first image analysis further comprises performing a Gaussian blur.

5. The method of claim 1, wherein the first image analysis further comprises identifying isolated pixel clusters and performing an iterative erosion on each cluster to separate connected clusters.

6. The method of claim 1, wherein the first algorithm comprises an active contour algorithm.

7. The method of claim 1, wherein the second image analysis further comprises identifying a polar body candidate in the image and determining the area, brightness, and/or circularity of the polar body candidate.

8. The method of claim 7, further comprising determining that the polar body candidate is a polar body as a function of any one of the area, brightness, circularity of the polar body candidate, and any combinations thereof.

9. The method of claim 1, wherein the non-linear microscope image is a two-photon microscope image; a multiphoton microscope image; a second harmonic generation microscope image; or a third harmonic generation microscope image.

10. The method of claim 1, wherein the non-linear microscope image is a fluorescence image of endogenous NADH inside the egg follicle.

11. The method of claim 10, wherein the egg follicle is exposed to conditions which maintain NADH concentration within the egg follicle to between 80% and 120% of the endogenous NADH concentration or which do not alter the NADH concentration within the egg follicle.

12. The method of claim 1, wherein the non-linear microscope image is a fluorescence image of endogenous FAD inside the egg follicle.

13. The method of claim 12, wherein the egg follicle is exposed to conditions which maintain FAD concentration within the egg follicle to between 80% and 120% of the endogenous FAD concentration or which do not alter the FAD concentration within the egg follicle.

14. The method of claim 1, further comprising a step of taking a plurality of non-linear microscope images of the egg follicle at a plurality of Z dimensions.

15. The method of claim 1, wherein the first and second image analyses are automated.

16. The method of claim 1, further comprising determining that an egg is mature if the egg is identified to have a polar body.

17. The method of claim 16, further comprising a step of selecting the mature egg for in vitro fertilization.

18. The method of claim 16, further comprising a step of performing in vitro fertilization with the mature egg.

19. The method of claim 1, wherein the egg is a human egg.

* * * * *